United States Patent
Stanley et al.

(10) Patent No.: US 11,058,207 B2
(45) Date of Patent: Jul. 13, 2021

(54) PRECISION APPLICATOR

(71) Applicant: The Procter & Gamble Company, Cincinnati, OH (US)

(72) Inventors: Scott Kendyl Stanley, Mason, OH (US); Mariana Saba, Singapore (SG); Andrew Paul Rapach, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 189 days.

(21) Appl. No.: 15/272,451

(22) Filed: Sep. 22, 2016

(65) Prior Publication Data

US 2017/0086566 A1    Mar. 30, 2017

Related U.S. Application Data

(60) Provisional application No. 62/232,477, filed on Sep. 25, 2015.

(51) Int. Cl.
| | |
|---|---|
| *A45D 44/00* | (2006.01) |
| *A61M 35/00* | (2006.01) |
| *A45D 40/26* | (2006.01) |
| *A61N 1/30* | (2006.01) |

(52) U.S. Cl.
CPC ........... *A45D 44/002* (2013.01); *A45D 40/26* (2013.01); *A45D 44/005* (2013.01); *A61M 35/10* (2019.05); *A61N 1/30* (2013.01); *A45D 2200/155* (2013.01); *A45D 2200/20* (2013.01); *A45D 2200/202* (2013.01); *A45D 2200/25* (2013.01); *A61M 2210/04* (2013.01); *A61M 2210/0606* (2013.01)

(58) Field of Classification Search
CPC .... A45D 44/002; A45D 44/005; A61M 35/00
See application file for complete search history.

(56) References Cited

U.S. PATENT DOCUMENTS

| | | | |
|---|---|---|---|
| 2008/0053476 A1 | 3/2008 | LaHood, Jr. | |
| 2009/0241242 A1* | 10/2009 | Beatty | A45D 44/002 2/206 |
| 2009/0280150 A1 | 11/2009 | Kamen et al. | |
| 2011/0123703 A1* | 5/2011 | Mohammadi | A61B 5/442 427/2.12 |
| 2011/0300196 A1 | 12/2011 | Fatemeh et al. | |
| 2012/0192884 A1* | 8/2012 | Nasu | A45F 3/18 132/200 |

(Continued)

FOREIGN PATENT DOCUMENTS

| | | |
|---|---|---|
| CN | 104385589 A1 | 3/2015 |
| CN | 104721061 A1 | 6/2015 |

(Continued)

OTHER PUBLICATIONS

Translation of CN 104997645.*
International Search Report and Written Opinion dated Nov. 10, 2016, 14 pgs.

*Primary Examiner* — Tatyana Zalukaeva
*Assistant Examiner* — Jessica R Arble
(74) *Attorney, Agent, or Firm* — Sarah M DeCristofaro

(57) ABSTRACT

A self-supporting applicator comprises a first structural element which is self-supporting and has a shape determined according to a target structure, the applicator further comprises an active agent.

12 Claims, 1 Drawing Sheet

(56) References Cited

U.S. PATENT DOCUMENTS

| | | | |
|---|---|---|---|
| 2014/0083878 A1* | 3/2014 | Tang | A61K 9/7061 |
| | | | 206/204 |
| 2014/0163445 A1* | 6/2014 | Pallari | A61K 8/0212 |
| | | | 602/43 |
| 2014/0350442 A1 | 11/2014 | Park et al. | |
| 2015/0250971 A1 | 9/2015 | Bachelder et al. | |
| 2015/0366327 A1* | 12/2015 | LaHood, Sr. | A45D 40/30 |
| | | | 264/109 |
| 2016/0089536 A1* | 3/2016 | Mohammadi | A61N 1/044 |
| | | | 604/20 |
| 2016/0235975 A1* | 8/2016 | Jung | A61N 1/30 |
| 2017/0231813 A1* | 8/2017 | Huang | A61F 7/034 |
| | | | 607/109 |

FOREIGN PATENT DOCUMENTS

| | | |
|---|---|---|
| CN | 104997645 A * | 10/2015 |
| DE | 3709885 | 8/1988 |
| EP | 2460435 A1 | 6/2012 |
| EP | 2730311 A2 | 5/2014 |
| JP | 2010163386 A | 7/2010 |
| JP | 2012075795 A | 4/2012 |
| JP | 2014181241 A | 9/2014 |
| KR | 20100007371 U | 7/2010 |
| KR | 20100128985 | 12/2010 |
| KR | 20130023528 A | 3/2013 |
| KR | 101342925 B1 | 12/2013 |
| WO | WO 2008/027465 A1 | 3/2008 |
| WO | WO 2009/137277 A2 | 11/2009 |
| WO | 2010033309 A1 | 3/2010 |
| WO | WO 2012039358 | 3/2012 |
| YU | 7902 A | 6/2005 |

* cited by examiner

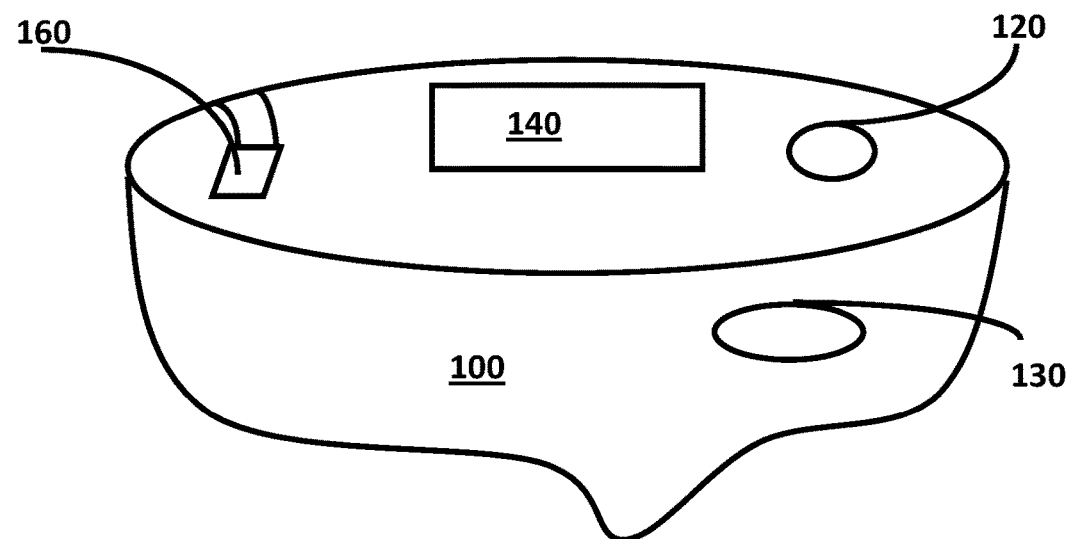
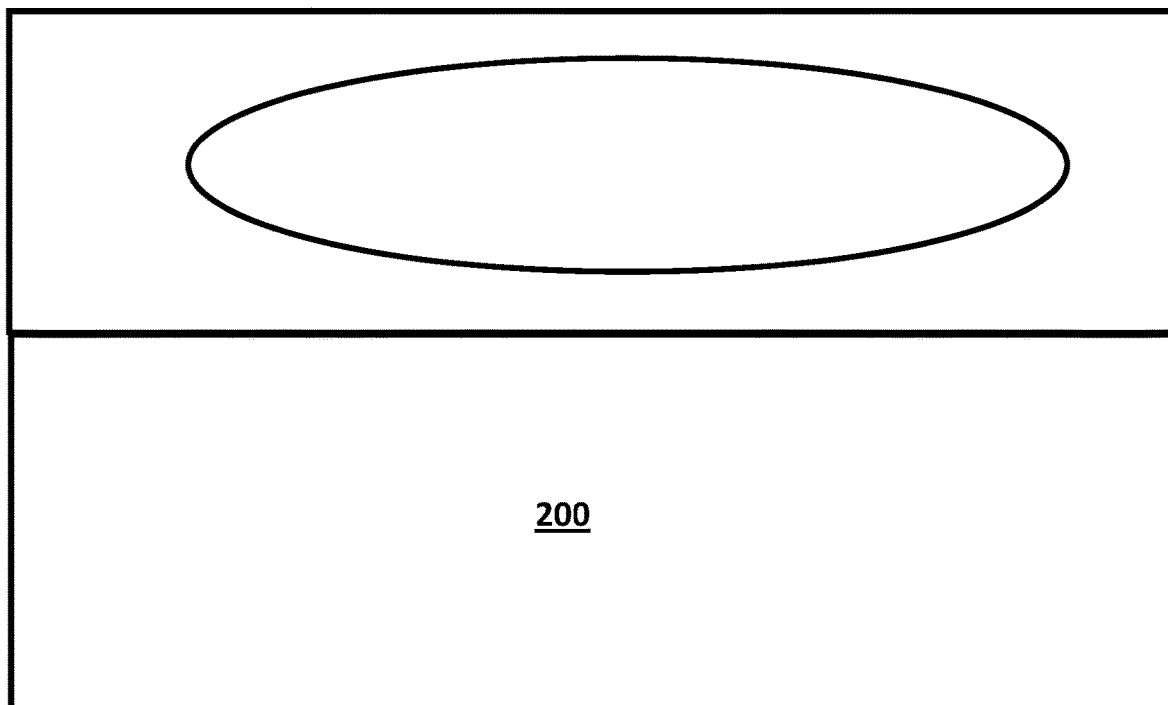

PRECISION APPLICATOR

FIELD OF THE INVENTION

The invention relates to implements for applying active agents to a target structure. The invention relates particularly to implements custom manufactured to precisely apply active agents to a target structure.

BACKGROUND OF THE INVENTION

Agents for affecting target structures are well known. Temperature affects may be induced by the application of hot or cold agents to the target. The appearance of a target may be affected by cosmetic and decorative agents. Electric current, voltages, and electric and magnetic fields may be applied to a target using local applicators. For biological targets, surface properties may be impacted by the use of topical application of moisturizers, medicaments and other treatment actives.

The effectiveness of the active agent may be impacted by the nature of the applicator available to facilitate the interaction of the active agent with the target structure. Typical applicators are less than precise with respect to their conformance to the target structure and the use of one-size fits all, or a few sizes fits all tends to compromise the actual performance of the active agent. What is needed is a precision application implement adapted to the geometry of the target structure to yield an improved active agent performance.

SUMMARY OF THE INVENTION

In one aspect, a self-supporting applicator comprises a first structural element which is self-supporting and has a shape determined according to a three-dimensional scan of a target structure, the applicator further comprises an active agent located according to a diagnostic scan of the target structure.

BRIEF DESCRIPTION OF THE DRAWINGS

Fig. provides a schematic perspective view of an embodiment of the invention.

DETAILED DESCRIPTION OF THE INVENTION

In one aspect the applicator comprises a first structural element having a shape determined according to a three-dimensional scan of a target structure. The first structural element may be self-supporting.

As used herein, the term self-supporting means that the element retains a substantial portion of the geometric relationships of a defined three-dimensional shape without the aid of external support structures when resting on a horizontal surface under ambient air pressure.

In one embodiment, the applicator of this invention includes an outer surface that may be dry and cleaner and easier for the consumer to handle. Due to the custom conformal fit to the target structure, for example a part of a human body, the applicator may be configured to have a low removal force. This may be accomplished through a combination of the conformal nature of the applicator and/or selected application of adhesive agents on controlled areas of the applicator, and/or other fastening means (for example, ear hooks, an elastic band, hook and loop straps, ties, etc.).

The three-dimensional scan of the target structure may be acquired using 3D scanners as are known in the art. An Artec Spider, available from the Artec Group, Palo Alto, Calif., is an exemplary 3D scanner. Using a smartphone such as an iphone 6 from Apple, Cupertino, Calif., and an app such as 123D Catch from Autodesk is another example. The three-dimensional scan of the target structure may be used as a whole or may be partitioned with only a portion of the total scan being used to define the shape of the structural element. Further, portions of the geometry derived from the scan may be removed or edited from the scan. For example, holes may be cut out from the scan data to aid with vision, breathing, or other body functions. Further, fiduciary markers, calibration markers, or alignment markers may be physically present and placed on or near the target surface to aid scanning technology in acquiring the geometry of the target in digital form.

In one embodiment, a physical negative of the target structure may be created using known methods such as curable conforming mesh structures, heat-shapeable mesh structures, casting compounds such as plaster of Paris or clay. The completed negative of the target structure may then serve as the target for the geometric scan to provide the geometry of the target structure after appropriate processing to yield the surface common to the negative and the actual target structure itself. In one embodiment, the target surface scan may be accomplished by any known physical probe scanning method such as contact profiling using a stylus.

The three-dimensional scan data may be used without alteration, or the geometry of the scan may be altered, such as with a digital data processing system, to yield a new geometry derived, but differing, from the target structure geometry. The geometric differences may be imparted to the new geometry for the purpose of enabling the structural element to be used in the application of mechanical compression or tension forces to the target structure. Mechanical devices may be added (e.g. levers, ratchets, moveable sections, and other known means) to impose forces upon the underlying target structure.

In one embodiment, one or more target structure contacting portions of the applicator possesses conformal fit to the target structure, while the geometry of one or more non-contacting portions of the applicator may be fabricated to provide additional function and/or appearance. Functional features may be incorporated to improve the ability of the applicator by a consumer, manufacturer, distributor or retailer to handle, place, or otherwise manipulate the applicator. Exemplary functional features include one or more: grips, handles, toggles & strap receiving elements. Additional functional features may help maintain the position of the applicator in relation to the target structure. Such features may include elements such as an elastic band or tie receiving, attaching or anchoring element.

With respect to appearance features, a non-target-structure-contacting portion of the applicator, such an externally-facing surface, or side of the applicator, may be altered any of a number of ways. Rather than incorporating the geometry of the scan, it may be shaped in the design of a selection of available designs, or a custom design provided by the consumer, manufacturer, distributor or retailer. Exemplary designs or likenesses of people, characters, and drawings available commercially which may be utilized with appropriate permissions include: the likeness of Elvis Presley, Darth Vader, Christie Brinkley, Wonder Woman, Scooby-Doo or other likenesses.

In one embodiment, interface geometry may be added to the geometry derived from the scan for the purpose of enabling the scan-derived geometry to be merged with the externally facing element.

In one embodiment, the target structure may be a body portion of a mammal such as a human face, or other portion such as a limb, joint, or portion thereof of a mammal.

In one embodiment, the target structure may be associated with an applicator selected from a limited array of applicators as an alternative to a precise custom applicator. As an example, a scan or other analysis of the target structure may be used to identify which element of a provided array of structures would be most suited to use for the application of an active to the target structure. The analysis could indicate that a particular applicator selected from the provided array of structures would provide sufficient precision in the application of the active to remove the need for a completely custom applicator.

The three-dimensional scan data may be further utilized as a diagnostic scanning tool by evaluating the data of the scan for geometric signatures identified as therapeutic indicators or triggers. The scan data may include visible light, variously polarized light, a particular narrow wavelength of light, ultra-violet, infrared, and/or ultra-sonic data associated with the scan of the target surface. The various data sets of the scan may be used as inputs to various diagnostic assessments for the purpose of identifying areas of opportunity for therapeutic treatment of the target structure.

As an example, a scan of a face may be analyzed to identify wrinkled skin, or the precursor geometric signatures known to indicate skin regions susceptible to or progressing toward a wrinkled condition.

The results of the diagnostic scan may be incorporated into the first structural element by way of indicia configured in the structure. The indicia may take the form of relative changes, or alterations, in the structure such as the texture, opacity, and/or color of the structural element at locations of opportunity identified from analysis of the diagnostic scan data.

The indicia may be used to indicate those portions of the surface of the structural element where a beneficial active material may be disposed such that placement of the structural element adjacent to the target structure may result in contact between the active material and the target structure.

In one embodiment, the location of the indicia may serve as deposition sites for active agents including therapeutic or cosmetic elements for the purpose of imparting therapeutic or cosmetic effects to the corresponding portions of the target surface. Such elements may be applied to the first structural element by hand, using a computer controlled robotic pick-and-place system, or by way of a three-dimensional printer. A 3Dn series or tabletop series conformal dispensing system, available from Nscript, Inc. of Orlando, Fla., is an exemplary printer for the deposition of the elements. For digitally instructed deposition systems of active agents to the first structural element, e.g. a three-dimensional printer, the actual indicia need not be printed or otherwise incorporated into the manufacture of the first structural element. In one embodiment, the indicia may be illustrated in a separate location from the custom applicator.

In one embodiment, the applicator and active agents are printed in the same process using a multiple extrusion head system, such as a Hyrel System 30 printer available from Hyrel LLC, of Norcross, Ga.

In one embodiment, the active agents may be embedded or infused within the applicator material itself, such as Cupron Enhanced materials available from Cupron of Richmond, Va.

In one embodiment, the applicator may be fabricated as a system of multiple layers. In this embodiment, an inner, surface contact layer may be comprised of a first polymeric or thermoplastic or thermoset material selected for the purpose of holding and subsequently transferring an active agent to the surface. The inner layer's first material may lend itself to be more conformable to the target structure's response to pressure and/or surface topography displacement. For the applicator of multiple layers, a second polymeric or thermoplastic or thermoset material may be used to fabricate an outer layer intended to provide support for the inner layer including the option to provide much or all the self-supporting structure for the multiple layer applicator. The outer layer may also hold various therapeutic implements such as electrical elements or thermal agents which work in concert with, or serve themselves as the active agents.

For the applicator of multiple layers, the first material and the second material may be the same material composition or may differ. For example the modulus, compressibility, and/or tackiness properties may singly be different or differ in any combination. Where the two materials differ: the outer material may be stiffer and/or possess a higher shore hardness value and/or a different color and/or a higher bending modulus than the first material of the inner layer. As another example the inner material may be softer and/or be more compressible and/or be tackier and/or be a different color and/or have a different modulus of elasticity than the material of the outer layer.

The multiple layers may be fabricated concurrently or in a sequential fashion with one of the layers being fabricated prior to the other layer(s). Interactive sequential fabrication is contemplated wherein after a portion of one layer is fabricated, and then a portion of another layer is fabricated followed by a return to fabricate a different portion of the original one layer. The active agents may be deposited at any time after the appropriate portion of the inner layer is fabricated.

In one embodiment, the outer layers may include one or more functional or appearance features. In one example, the inner layer may be only partially, or not at all self-supporting, while the outer layer may be substantially or completely self-supporting.

The active agents may be uniform, zoned, or varied in composition pixel by pixel or voxel by voxel. For example, the one of more active agent may be applied or deposited onto the custom applicator to create a perfectly uniform thickness film. Alternately, the active agent may be applied to the custom applicator in a zoned fashion, such as a first active agent in the T zone of the face and a second active agent in the U zone of the face.

In one embodiment, the active agent may be uniformly coated onto the applicator so that when applied to the target surface, it provides perfectly uniform coverage over the entire area defined by the custom applicator.

In one embodiment, the custom applicator is designed for use on the face and eye holes are removed from the custom applicator. Due to the self-aligning nature of the custom applicator (i.e.—because it is perfectly fitting it can only fit one way) active agents may be deposited on the custom applicator and brought into contact with the face very near the skin-eye border.

For covering a particular region of the body such as the face, whole face coverage can be achieved. Both the extent of coverage in terms of percentage area covered and the uniformity of the coating in terms of the variation in amount deposited per surface area are improved by this invention. For example, for a given individual's face, the total surface area with eyes and mouth closed can be measured from a 3D scan as 371.1 cm2. This may be considered as the total surface area. Removing the eyes, nostrils, and mouth from consideration, the amount of surface area is then 343.1 cm2, which may be referred to as surface area of interest. 100%, 90%, 80% or any other percentage of the surface area of interest of the custom applicator may be coated to deliver the corresponding percentage of area coverage on the target surface.

spacing. For the custom applicator of this invention, the mask was fit to a specific individual so that dry area could precisely be minimized to be equal to or nearly equal to the excluded area.

Measurements of the prior art substrate mask vs. the custom applicator of this invention are shown in the table below. Additionally, a fit ratio defined as the ratio of the excluded area to the dry area was determined for each mask. For a perfectly fitting custom applicator, the fit ratio will be equal to, or near 1.0. As the fit becomes poorer with different masks, the ratio will decrease to lower values below 1.0. The custom applicators of this invention can be configured with fit ratio of about 1.0, about 0.9, about 0.8, about 0.7, or any value between 0 and 1.0.

|  | L eyeball (square pixels) | R eyeball (square pixels) | mask dry area L side (square pixels) | mask dry area R side (square pixels) | E total excluded area | d total dry area | E/d fit ratio |
|---|---|---|---|---|---|---|---|
| prior art mask | 39823 | 42011 | 77197 | 102424 | 81834 | 179621 | 0.456 |
| custom applicator (this invention) | 36579 | 39008 | 36579 | 39008 | 75587 | 75587 | 1.0 |

In one embodiment, these eye holes, nostrils, and mouth opening can be manually removed from the scan data, the wire mesh, or the CAD solid. In another embodiment, automated routines can automate the identification and removal of these regions.

In one example, the active agents are coated all of the way to the eye opening of the custom applicator. In this embodiment, the active agent is then brought into contact with the skin and active agents are precisely delivered to the skin very near the eye. This can have the advantages of being easier to apply active agents near the eye, proving safer application near the eye, and providing better uniformity near the eye. The active agents may then optionally be rubbed into the skin by finger after removal of the custom applicator.

In one example, the fit of a prior art commercial substrate mask was compared to a custom applicator mask according to one embodiment of the invention. In this example, a two-piece mask called the ADVANCED NIGHT REPAIR® mask from Estee Lauder, of New York, N.Y. was used. This is a substrate mask that contains a substrate material soaked in active agents and has holes for eyes and mouth as well as openings for the nostrils. The following process was used to compare the coverage and the fit: first the substrate mask is applied to a face. A photograph #1 was taken straight on including a scale marker capturing the substrate mask as worn on the face. Second, the substrate mask was removed and the custom applicator mask of the embodiment was worn on the face and a similar photograph #2 was taken. Then, both photographs were imported into IMAGEJ® software, available from the National Institute of Health, for image analysis. The freehand region of interest tool was used to define excluded areas where no treatment was desired, i.e. in this example the right and left eyeball, and measure the area of excluded area in square pixels. The excluded area was defined to include both the bottom and top eyelids. Next, the dry area was measured using the same methodology. In this example, the dry area was defined by the eye holes in both masks. For the prior art substrate mask, the dry area was rather large because so called "one size fits all" masks must use a suitably large eye opening to accommodate a range of face sizes, shapes, eye sizes, and eye In another example, the custom applicator may cover more of the total available treatment area than a prior art mask. The total surface area of the face from hairline to underneath the jawline may be measured by 3D scanning The non-treatment areas (i.e. excluded areas) such as the eyes, nostrils, lips may all be precisely removed from the custom applicator or active agents may be omitted from these regions of the custom applicator. Because the custom applicators of this invention are created based on the geometry of that target surface, they can be made to overlay and or deliver benefit agents to 100% of the intended treatment area (where the treatment area is defined as the total surface area minus the excluded area). Further the custom applicator can be made to overlay and or deliver benefit agents to any other percentage of the intended treatment area, such as about 99%, about 90%, about 80%, about 70% or any number between 0 and 100 percent.

In one embodiment of the applicator of multiple layers, the outer layer of the applicator may be selected from a limited array of outer layers into which a custom fit inner layer is fabricated. In one embodiment, the inner layer may be fabricated with an external surface shaped or containing features to permit it to attach or adhere to an outer layer of the applicator. In this embodiment, the outer layer may be selected from a limited array of pre-determined outer layers. As an example, at least a portion of the external surface shape of the inner layer conforms to at least one or more corresponding portions of the inner surface of the outer layer such that the two layers adhere to one another as is, or with the assistance of an adhesive, tacky resin, mechanical fastening or other means for at least releasably fastening the two layers together. As another example, mechanical fasteners or interlocks may be included with one attachment element affixed to, or comprising a portion of the external surface of the inner layer, and a corresponding mating attachment element affixed to, or comprising one or more corresponding portions of the inner surface of the outer layer. One example, of many known examples, is a snap fastener (also called press stud, popper, snap or tich) which comprises a pair of interlocking discs, made out of a metal or plastic, commonly used in place of buttons to fasten clothing and for similar purposes. The two interlocking (interference fit) discs make up a useful attachment system wherein the first disc is the one attachment element and the second disc is the mating attachment element.

The outer layer selected from the limited array of predetermined outer layers may be reusable. A portion or the entirety of an inner layer may be removed or separated from the outer layer and discarded after use. Subsequently, at least a portion or a complete new inner layer may be affixed to the reusable outer layer. The new portion or complete inner layer may be derived from the original scan(s) or may be from a different scan.

Additionally, the custom applicator may be made from occlusive or barrier materials that limit the transport of water, water vapor, or gasses through it. The occlusive properties of the custom applicator may be characterized by measurements of WVTR or MVTR (water vapor transmission rate and moisture vapor transmission rate, respectively). The MVTR is the steady state rate at which water vapor permeates through a film at specified conditions of temperature and relative humidity, and can be determined using ASTM F1249. The custom applicators described herein in one embodiment may have MVTR in the range of about 40 g/m2 dy to about 0.1 g/m2 dy. In another embodiment, the custom applicator may be more breathable and have MVTR values greater than about 40 g/m2 dy.

Active agents may comprise active ingredients, carriers, chassis, emulsions, hydrogels, adhesives, process aides (such as thickeners, rheology modifiers, etc.). Active agents may further comprise a release layer to help active agents transfer from the applicator to the target surface. Some examples of active agents include but are not limited to: moisturizer, anti-aging, anti-wrinkle, skin tone control, anti-irritation, sensates (e.g. menthol), heating or cooling chemistries, skin tightening, hair removal, hair regrowth, fungicide, antibacterial, antiviral, copper ion eluting (such as from Cupron of Richmond, Va.), antioxidants, vitamins, sunscreen, rejuvenation agents, wound healing agents, sebum management agents, astringents, exfoliates, anti-inflammatory, leave on, overnight, dry skin, itchy skin, cracked skin, peptides, acne, scar treatments, sore muscles, medicaments including pharmacological actives to treat disease states or other acute or chronic issues such as eczema, rashes, acne, cancer, cold sore, Psoriasis, Rosacea, Vitiligo, warts, diaper rash, Herpes, fungal nail infection, Actinic Keratosis, ulcers, corns, calluses, shingles, poison ivy, and insect bites. Further, the medicaments, including pharmacological actives, can go beyond topical effect and be designed for transdermal delivery of an active into the bloodstream or other internal tissue—such as in many therapies. Examples of therapies, both prescribed and un-prescribed include: nicotine and hormone supplements.

Exemplary active agents for cosmetic changes to the target structure include: fingernail polish, toenail polish, deodorant, primer, lipstick, lip gloss, lip liner, lip plumper, lip balm, lip conditioner, lip primer, lip boosters, concealer, foundation, powder, rouge, blush, blusher, contour powder/creams, highlight, bronzer, mascara, eyeliner, abd setting materials, scents, perfume or fragrance compositions (e.g. essential oils).

In one embodiment, one or more scents, perfume or fragrance compositions, antiperspirants, or deodorants, may be applied to the applicator for subsequent deposition to the target structure. However, a portion, or all, of the included one or more scents, perfume or fragrance compositions may act as experience agents. The experience agent provides a smell in the environs of the applicator when in use. For example, the smell provided by a fragrance to suggest an outdoor flower garden aroma may he desirable when applying cosmetic agents to the face of a consumer/wearer. Experiential agents need not necessarily be located on the target structure contact surface of the applicator. The agents may be located in a region not in contact with the structure, such as on a non-contacting portion of the application side of the applicator or anywhere on any applicator side that is non-contacting to the t structure. The experience agent may be selected to accompany a selected appearance feature. In one embodiment, the indicia may comprise the active agent deposited upon the first structural element without alterations to the relative color or texture of the application site.

The active or experience agents may be releasably deposited upon the first structural element such that the active agents will be substantially transferred from the first structural element to the corresponding locations of the target surface as or after the first structural element is brought into the proximity of, or actual contact with, the target structure.

The active agents may be present in a gel form, fiber form, film form, liquid, solid, or any other form and present either upon the surface of or within the applicator.

In another example, a baseline scan may be made of a knee joint when there are no issues with the joint. Subsequent to the baseline scan, at a time when there is an issue with the joint, a subsequent scan may be made to identify changes in the geometry and surface temperature of the respective portions of the joint due to inflammation, or other causes. The scans may then be used for the purpose of generating a geometry associated with the joint and taking into consideration the baseline and current state of the joint. The geometry may be used to create a first structural element precisely matching the current state or modified from the current state using data from the baseline scan to create a modified geometry with the intention of selectively applying compression to the inflamed joint upon application.

Similarly, a baseline diagnostic scan may be made for comparison purposes at a later time as part of an ongoing regimen.

The structural element may then serve as a target structure contact surface and may be combined with an outer shell element, or second structural element, having a geometry wherein there is an interface portion matched to a portion of the first structural element such that the outer shell and first structural element may be combined to form a hollow shell having an inner surface associated with the target surface and an interior volume derived from a therapeutic intent associated with the scan data for the joint. The combination may define a cavity between the elements. The location and volume of the cavity may be defined using data from the diagnostic scan.

In this example, the cavity of the combination shell may then be at least partially filled with any active agent; examples include heating or cooling agents for the purpose of the precise application of relative heating or cooling of portions of the affected joint determined according to the scan data. The first structural and/or outer shell elements may be fabricated to include insulating portions, or to have structural features adapted for the subsequent installation of insulating elements to control those portions of the target structure and/or external environment subjected to the effects of the heating or cooling agents. In this manner, the exposure to the therapeutic temperature active agent may be precisely limited to only the portions of the target structure where such exposure is desired.

In one embodiment, the face may be scanned for geometry and also scanned for type, location, and amount of active elements. Then, a self supporting 3D mask may be printed with active elements on the inner surface for delivery to a consumer's face.

In another example, the face may be scanned for geometry and then the geometry processed to create a mechanical treatment plan for the face. The applicator can then through mechanical means alone and/or by using active elements apply forces to the face to hold the face into a new geometry, thus providing a face lift mask.

The first structural element and outer shell elements may be fabricated using either traditional machining methods, or the elements may be fabricated using additive manufacturing methods such as stereo-lithography or selective powder sintering techniques.

The elements may be created using any polymer, thermoplastic or thermoset material. Examples include ABS, Nylon, polyolefin, polyester (e.g. PET, PLA), thermoplastics or elastomeric materials to impart an elastomeric nature to the elements. Photopolymer (SLA or continuous liquid interface printing, i.e. CLIP), sintered particles (e.g. SLS), binderjet particles, or any other methods of additive manufacturing may also be used. The flexibility of the elements may also be altered by the inclusion of physical hinge elements in the design geometry of the elements. Hinges or other breaks in the applicator may be used to facilitate how the applicator is placed around a body part, such as around the elbow.

The target structure may be evaluated to define a level of flexibility desired in the first structural element and/or the combination of the first structural element and the outer shell element. The defined flexibility may subsequently be utilized to inform the element design in addition to the materials and fabrication technique selection for the elements in order to provide elements created with consideration for the flexibility or range of motion etc. of the underlying target structure.

The first structural element may comprise component elements enabling the application of electric current, voltage and/or electrical or magnetic fields to portions of the target structure. Electrodes, electrical coils and other necessary components may be disposed upon the surface of the element or embedded or printed within the element such that, with the addition of a power sources such as a battery, photovoltaic solar cell, line voltage or other electrical power source, the desired energy may be applied to the target.

The geometry of the applicator may be varied from that of the scanned target to provide accu-pressure benefits via the applicator. Accu-puncture elements may be incorporated into the applicator directly or apertures associated with desired accu-puncture sites may be provided as part of the customized applicator.

In one embodiment, the applicator could have integrated electronic components to serve a variety of purposes. For example, the applicator could have integrated and printed electrical traces. These traces could connect a power source (such as a coin cell battery, printed battery, fuel cell, plug to the wall, or other power source) to actuators, sensors, or energy emitters. Example of actuators and energy emitters include LEDs, vibration sources, actuators to locally create a displacement to apply pressure, massage elements, thermoelectric heating and cooling elements, and electromagnets. The applicator may include structures enabling the attachment of such power sources and energy emitters as well.

In one embodiment, the integrated electronic components may be integrated into the outer layer and/or the inner layer of the applicator of multiple layers. Further, integrated electronic components may provide an experience function, analogous to an experience agent, while using the applicator. Examples include connectivity to smartphone or audio devices such that music may be played using audio speaker elements integrated into a facial applicator mask during applicator use. As another example, they may include transmission elements, connection to or parts of or a complete virtual reality system. For the example of a facial treatment applicator (e.g. a mask) the wearer can enjoy virtual reality content during the use of the applicator.

In one embodiment, the applicator may be provided as part of a consumer product kit. The kit may comprise the applicator element, or elements, and one or more active agents. The active agents may be predisposed upon the first structural element, or may be provided in a form suitable for application to the structural element by the consumer/user of the kit elements. The kit may further include a key (map) indicating the points of deposition for the active agent upon the surface of the structural element according to indicia, or as an alternative to the indicia.

The elements of the kit may be provided in a plurality of ways. In one embodiment, the structural element and active agent may be prepared, frozen, and provided in combination as a frozen article to be applied frozen, or to be thawed and used. In one embodiment, the structural element and active agent may be combined and sealed to shield the active agent from environmental effects. The structural element and active may be provided enclosed in a sealed pouch or the perimeter of the structural element may be adhered to a film element to enclose the active agent within a chamber shielded from the external environment.

As shown in the Fig: a kit 1000 comprises a first structural element 100. The first structural element 100, comprises indicia, 120, an active agent 130, an insulating element 140 and an electrical element 160. The kit 1000 further comprises a second structural element 200 configured to receive the first structural element resulting in the creation of a cavity (not shown) between the first and second structural elements.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A self-supporting applicator comprising:
a first structural element having a shape determined from a target structure, wherein the first structural element comprises a surface contact layer and a support layer, wherein the surface contact layer is made from a first polymeric material and the support layer is made from a second polymeric material, and
an active agent disposed on the first structural element, wherein the active agent is made from an active agent material,
wherein the active agent material, the first polymeric material, and the second polymeric material are different materials,
wherein the WVTR of the first structural element is less than about 40 g/m2 dy;
a second structural element, at least a portion of the second structural element comprising a shape determined from a three-dimensional scan of the target structure, the second structural element disposed adjacent to the first structural element, wherein at least one spatial cavity having a defined volume and location, the cavity volume at least partly defined by portions of the first and second structural elements, is disposed between the first and second structural elements, wherein the volume and location of the at least one spatial cavity is determined from the three-dimensional scan;
wherein the active agent is disposed in the at least one spatial cavity.

2. The self-supporting applicator according to claim 1, wherein the shape of the first structural element is determined according to a scan of the target structure.

3. The self-supporting applicator according to claim 1, wherein the active agent is disposed according to a diagnostic scan of the target structure.

4. The self-supporting applicator according to claim 1, the first structural element further comprising indicia located according to a diagnostic scan of the target structure.

5. The self-supporting applicator according to claim 1 wherein the active agent is releasably attached to the applicator.

6. The self-supporting applicator according to claim 1, wherein a portion of the applicator comprises an elastomeric material.

7. The self-supporting applicator according to claim 1, further comprising an insulating element disposed adjacent to a surface of the first structural element.

8. The self-supporting applicator according to claim 1, the applicator comprising flexibility determined according to properties of the target structure.

9. The self-supporting applicator according to claim 1, wherein the geometry of the first structural element is determined according to the three-dimensional and a diagnostic scan.

10. The self-supporting applicator according to claim 1, further comprising at least one element adapted for the application of an active agent selected from the group consisting of: electric current, electric voltage, an electric field, a magnetic field, and combinations thereof, to the target structure.

11. A kit for the application of an active agent to a target structure, the kit comprising:
a self-supporting applicator comprising:
a first structural element having a shape determined from a target structure, wherein the first structural element is made from a first material comprising a polymeric material, wherein the WVTR of the first structural element is less than about 40 g/m2 dy, wherein the first structural element comprises indicia located according to a diagnostic scan of the target structure;
an active agent disposed on the first structural element according to the indicia, wherein the active agent is made from a second material, and wherein the first material is different than the second material;
a second structural element, at least a portion of the second structural element comprising a shape determined from a three-dimensional scan of the target structure, the second structural element disposed adjacent to the first structural element, wherein at least one spatial cavity having a defined volume and location, the cavity volume at least partly defined by portions of the first and second structural elements, is disposed between the first and second structural elements, wherein the volume and location of the at least one spatial cavity is determined from the three-dimensional scan;
wherein the active agent is disposed in the at least one spatial cavity; and
one or more active agents provided in a form suitable for application to the self-supporting applicator by a user.

12. The kit according to claim 11, wherein the shape of the first structural element is determined according to a scan of the target structure.

* * * * *